United States Patent [19]

Cabri et al.

[11] Patent Number: 5,180,758
[45] Date of Patent: Jan. 19, 1993

[54] PROCESS FOR PREPARING ANTHRACYCLINONES

[75] Inventors: Walter Cabri, Milan; Ilaria Candiani, Busto Arsizio; Silvia De Bernardinis, Milan; Franco Francalanci, Novara, all of Italy

[73] Assignee: Farmitalia Carlo Erba S.r.l., Milan, Italy

[21] Appl. No.: 743,373
[22] PCT Filed: Feb. 28, 1990
[86] PCT No.: PCT/EP90/00334
§ 371 Date: Aug. 26, 1991
§ 102(e) Date: Aug. 26, 1991
[87] PCT Pub. No.: WO90/09974
PCT Pub. Date: Sep. 7, 1990

[30] Foreign Application Priority Data

Mar. 2, 1989 [GB] United Kingdom ............... 8904794

[51] Int. Cl.⁵ ............................................. C07C 50/22
[52] U.S. Cl. ..................................... 552/201; 552/206
[58] Field of Search ............................. 552/201, 206

[56] References Cited

U.S. PATENT DOCUMENTS 5,103,029  4/1992  Cabri et al. ........................ 552/207

FOREIGN PATENT DOCUMENTS 0288268 10/1988 European Pat. Off. .
0337665 10/1989 European Pat. Off. .
0354995  2/1990 European Pat. Off. .

OTHER PUBLICATIONS

J. Chem. Soc., Chem. Commun., 1987, R. E. Dolle et al.: "Palladium catalysed alkoxycarbonylation of phenols to benzoate ester", pp. 904–905.
Tetrahedron Letters, vol. 27, No. 45, 1986, Pergamon Journals Ltd, (GB), S. Cacchi et al.: "Palladium-catalyzed triethylammonium formate reduction of aryl triflates. A selective method for the deoxygenation of phenols", pp. 5541–5544.

Primary Examiner—Marianne M. Cintins
Assistant Examiner—Kimberly J. Kestler
Attorney, Agent, or Firm—Oblon, Spivak, McClelland, Maier & Neustadt

[57] ABSTRACT

4-substituted anthracyclinones of general formula (I):

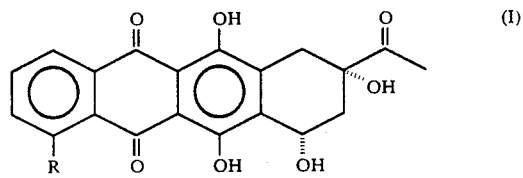

wherein R represents a hydrogen atom or a COOR₁ group in which $R_1$ may be a hydrogen atom or an optionally substituted $C_1$–$C_{10}$ alkyl group, which are intermediates in the preparation of antitumor anthracycline glycosides, are prepared by:

(i)(a) reacting a 4-demethyl-4-sulfonyl-7-deoxy-13-dioxolanyl daunomycinone of formula (V):

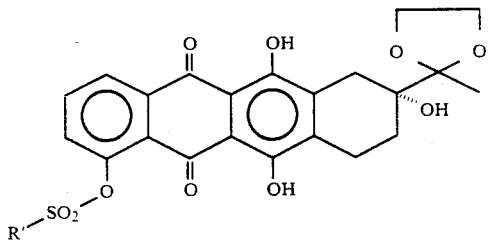

wherein R' represents an alkyl group having from 1 to 10 carbon atoms optionally substituted by one or more halogen atoms or an aryl group optionally substituted by halogen, alkyl, alkoxy or nitro, in a reducing environment with a catalytic amount of a compound of formula (VIII):

$ML_nL'_m$ wherein M represents a transition metal atom, L and L', which may be the same or different, each represent an anion or a neutral molecule and n and m may vary from 0 to 4, such as to obtain a compound of formula (VII):

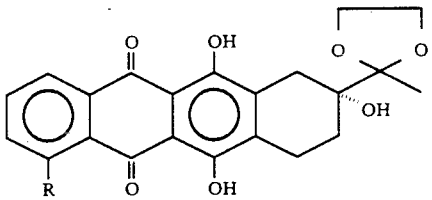

wherein R represents hydrogen; or (b) carbonylating a 4-demethyl-4-sulfonyl-7-deoxy-13-dioxolanyl daunomycinone of formula (V) as defined above, with carbon monoxide in the presence of a nucleophile $R_1OH$ wherein $R_1$ is as defined above, an organic or inorganic base and as catalyst a compound of formula (VIII) as defined above, such as to obtain a compound of formula (VII) as shown above wherein R represents a $COOR_1$ group; and (ii) introducing an α-hydroxy group at the 7-position and removing the 13-oxo protecting group by acid hydrolysis from the resultant compound of formula (VII).

9 Claims, No Drawings

PROCESS FOR PREPARING ANTHRACYCLINONES

The present invention relates to a process for preparing anthracyclinones of the general formula (I):

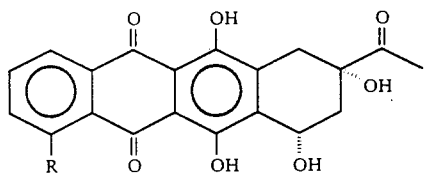

wherein R represents a hydrogen atom or a $COOR_1$ group in which $R_1$ may be a hydrogen atom or a straight or branched alkyl group having from 1 to 10 carbon atoms optionally substituted at one or more carbon(s) in the chain with inert groups such as an aryl group, an alkoxy group, an ester or an amido group.

Accordingly, the present invention provides a process for the preparation of an anthracyclinone of formula (I), which process comprises:

(i) (a) reacting a 4-demethyl-4-sulfonyl-7-deoxy-13-dioxolanyl daunomycinone of formula (V):

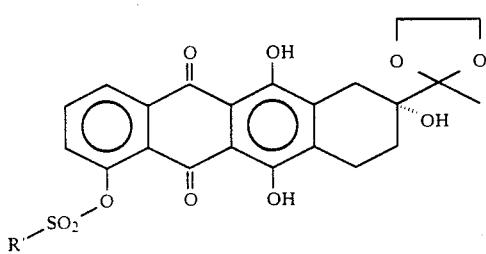

wherein R' represents an alkyl group having from 1 to 10 carbon atoms optionally substituted by one or more halogen atoms or an aryl group optionally substituted by halogen, alkyl, alkoxy or nitro, in a reducing environment with a catalytic amount of a compound of formula (VIII):

$$ML_nL'_m$$

wherein M represents a transition metal atom, L and L', which may be the same or different, each represent an anion or a neutral molecule and n and m may vary from 0 to 4, such as to obtain a compound of formula (VII):

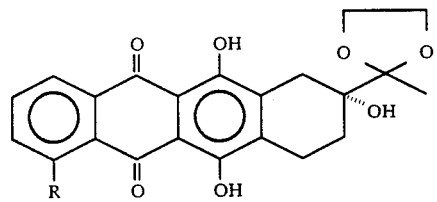

wherein R represents hydrogen; or (b) carbonylating a 4-demethyl-4-sulfonyl-7-deoxy-13-dioxolanyl daunomycinone of formula (V) as defined above, with carbon monoxide in the presence of a nucleophile $R_1OH$ wherein $R_1$ is as defined above, an organic or inorganic base and as catalyst a compound of formula (VIII) as defined above, such as to obtain a compound of formula (VII) as shown above wherein R represents a $COOR_1$ group; and (ii) introducing an α-hydroxy group at the 7-position and removing the 13-oxo protecting group by acid hydrolysis from the resultant compound of formula (VII).

In the definitions, an alkyl group such as $C_1$–$C_{10}$ alkyl is typically $C_1$–$C_4$ alkyl, for example methyl. An aryl group is preferably phenyl. An alkoxy group is typically $C_1$–$C_4$ alkoxy. An ester group is, for example, ($C_1$–$C_4$ alkoxy)carbonyl. The amido group is generally carbamoyl. Halogen includes F, Cl and Br. Typically m+n is at least 1, for example 1, 2, 3 or 4.

The process for the preparation of compounds of general formula (I) is illustrated by the following reaction scheme 1. The starting material shown there, 4-demethyl-7-deoxy daunomycinone (II), may be prepared by total chemical synthesis as described in U.S. Pat. No. 4,046,878:

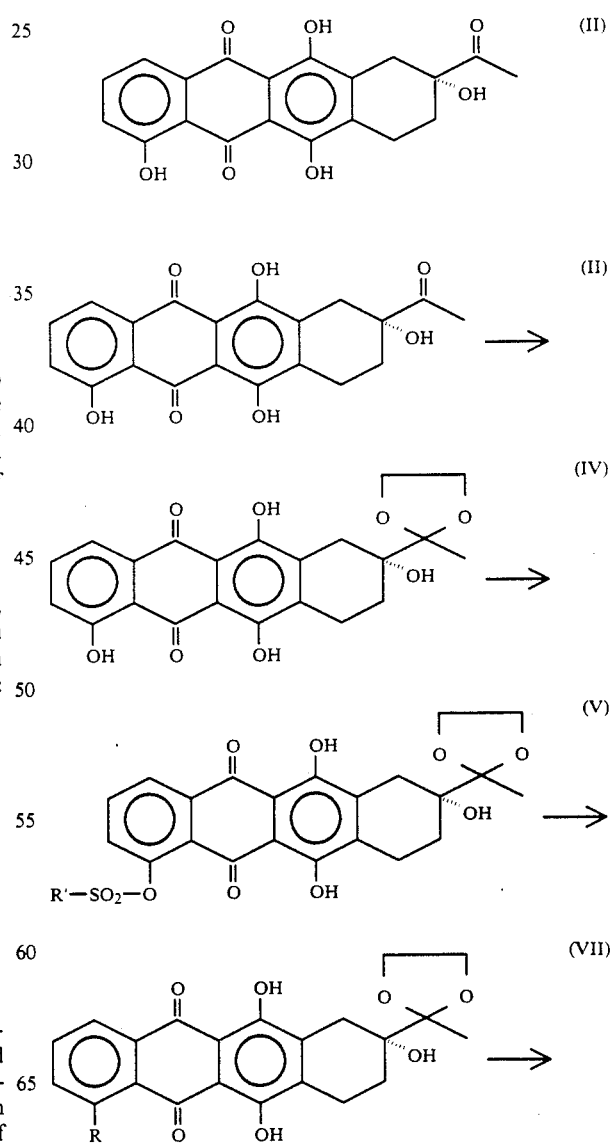

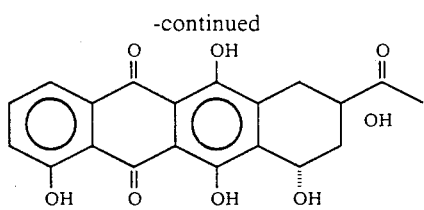

(I)

More conveniently (II) can be obtained by C4—OCH₃ demethylation of the naturally occurring daunomycinone (III) followed by hydrogenolysis of the 7α-hydroxyl group

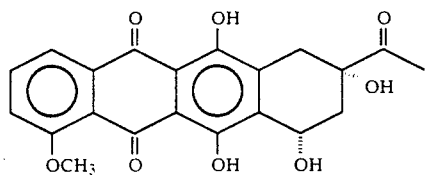

(III)

Compound (II) is then protected at the C13 keto group by reaction with ethylene glycol to give (IV)

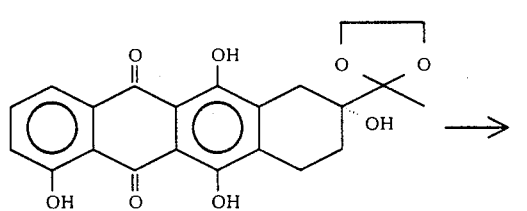

(IV)

and selectively sulfonated in position C4—OH (V):

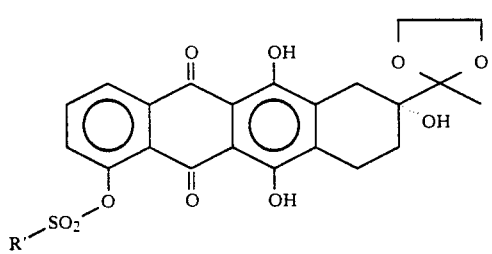

(V)

The sulfonating agent is a sulfonyl compound of formula (VI):

R'SO₂X   (VI)

wherein X may be a halogen atom, a OSOR' group, an imidazolide, a NH(C₆H₅)(R'SO₂) or another group capable of reacting with a phenol to give a sulfonate, and R' represents an alkyl group having from 1 to 10 carbon atoms, a halo or polihalo alkyl group or an aryl group optionally substituted by halogen atom(s), alkyl, alkoxy or nitro groups. Preferred groups which R' may represent are: trifluoromethyl, 4-fluorophenyl and 4-tolyl.

According to the process of the invention compound of formula (V) is

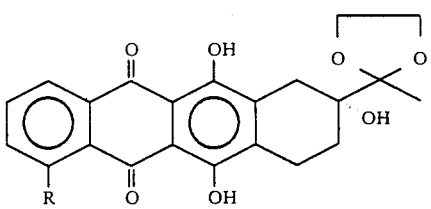

(VII)

transformed into (VII) by treatment in an appropriate solvent with a compound of formula (VIII) (hereunder referred to as catalyst):

$ML_nL'_m$   (VIII)

wherein M represents a transition metal atom, L and L', same or different, may be an anion as Cl⁻ or CH₃COO⁻ or a neutral molecule as a solvent molecule, a mono or a di-phosphine, a phosphite or a diamine; n and m may vary from 0 to 4. Preferred transition metal atoms which M may represent are palladium or nickel. Preferred groups which L and/or L' may represent are triaryl phosphines such as triphenyl phosphine and tritolyl phosphine or chelating diphosphines such as 1,3 diphenylphosphino propane and 1,1' bis-(diphenylphosphino)ferrocene.

In particular, 4-demethoxy-7-deoxy-13-dioxolanyl daunomycinone ((VII), R=H) is obtained by treating (V), under an inert atmosphere, with the catalyst, either preformed or generated "in situ" from suitable precursors, in the presence of a reducing system which is able to act as a formal hydride donor. A suitable reducing system, under the conditions of the invention is a trialkylammonium formate formed "in situ" by addition of formic acid and a trialkylamine. Reaction is typically at 60° C.

Alternatively compounds of formula ((VII), R=COOR₁) are obtained by treating (V) under a carbon monoxide atmosphere, with the catalyst, either preformed or generated "in situ" from suitable precursors, in the presence of a nucleophile R₁OH, wherein R₁ is as defined above, and a base. Suitable bases are trialkylamines and alkali or alkaline earth carbonates or hydroxides.

The temperature of the reaction is typically from 0° to 150° C. The catalyst (VIII) is generally used in a molar ratio with respect to (V) from 1:1 to 1:10000, preferably from 1:20 and 1:1000. The CO pressure may vary from 1 to 100 atm., preferably from 1 to 10 atm.

The 7α-hydroxyl group is then introduced into the compounds of formula (VII) and the ketal group removed to give the final compounds of formula (I). The introduction of the 7α-hydroxyl group may be performed according to the method described by C. M. Wong et al., Can. J. Chem. 51, 446, (1973): brominating compounds (VII) at the C7 position and hydrolysing the 7-bromo and the 13-ketal groups to give compounds of formula (I).

Typically the α-hydroxy group is introduced at the 7-position of the compound of formula (VII), the 13-dioxolanyl protecting group is removed by acid hydrolysis at 0° C. with trifluoroacetic acid, and the obtained crude product is purified by chromatography on a silica gel column using as eluent system chloroform-acetone. When R is hydrogen, the eluent system may be chloroform-acetone (9:1 v/v). For R as $COOR_1$, the system may be chloroform-acetone (95:5 v/v).

Although the use of transition metal catalysis for both hydrogenolysis and carbonylation of aryl sulfonates has been known for years it is new in anthracycline chemistry. The process of the present invention, starting from a common sulfonate of formula (V) allows several valuable intermediates of general formula (I) to be synthesised which are otherwise accessible only by individual total synthesis. Moreover, when the starting material (II) is obtained from the naturally occurring daunomycinone (V), the present invention allows to the target molecules of general formula (I) to be synthesised in high yield and without optical resolution steps. The compounds (I) are intermediates in the preparation of antitumor anthracycline glycosides.

The present invention will be now more fully described by means of the following Examples, which are provided merely for purposes of illustration and are not intended to limit the present invention.

EXAMPLE 1

4-Demethyl-7-deoxy-13-dioxolanyl daunomycinone (IV)

To a suspension of 13 g (35.3 mmol) of 4-demethyl-7-deoxy daunomycinone in 400 mL of benzene were added 30 mL of ethylene glycol and 0.3 g of para-toluensulfonic acid. The reaction mixture was refluxed with azeotropic removal of water for ca. 6 hours, then cooled to room temperature. The solid was recovered by filtration and washed with water and ethanol to give, after drying, 13.1 g of (IV). The product showed on HPLC analysis to be of 98.6% purity.

HPLC analysis: Column: MERCK RP 18/7 μm (250×4.2 mm),

| A-0.01M sodium heptansulfonate/0.02M phosphoric acid | 6 |
| Acetonitrile | 4 |
| B-Methanol | 7 |
| Acetonitrile | 3 |

Gradient: from 20% B to 70% B in 25 min,
Flow rate: 1.5 mL/min,
Detector: UV at 254 nm.
$^1$H-NMR 300 MHz (in $CDCl_3$): $\delta=1.46$ (3H, s), 1.50-2.20 (3H, m), 2.71-3.22 (4H, m), 4.08 (4H, s), 7.28 (1H, dd, J=8.2,1.2 Hz), 7.67 (1H, t, J=8.2 Hz), 7.86 (1H, dd, J=8.2,1.2 Hz), 12.31 (1H, s), 12.84 (1H, s), 13.67 (1H, s) M.S. : m/z=412 ($M^+$, base peak).
$[\alpha]_D^{20}$ (c=0.1 in dioxane)= $-76°$.
U.V. (in EtOH): $\lambda=528,514,492,293,255,236,204$ nm; $\lambda max=255$ nm.
I.R. (Nujol mull):3420,1590,1518 $cm^{-1}$.
TLC on Kieselgel plate F 254 (Merck) using chloroform/acetone (9/1 by volume): Rf=0.62.

EXAMPLE 2

4-Demethyl-4-trifluoromethansulfonyl-7-deoxy-13-dioxolanyl daunomycinone (V; R'=$CF_3$)

To a solution in pyridine (110 mL) of 1.1 g (2.7 mmol) of (IV), 2.3 mL (13.2 mmol) of diisopropylethylamine and 0.33 g (2.7 mmol) of 4-dimethylaminopyridine, cooled at 0° C., were added 1.4 mL (8.3 mmol) of trifluoromethansulfonyl anhydride and the reaction mixture was stirred for 1 hour at room temperature. The reaction mixture was then cooled to 0° C. and added with 500 mL of methylene chloride and 300 mL of 10% hydrochloric acid. The organic phase was washed with water, dried over sodium sulfate and the solvent evaporated under reduced pressure to leave a solid which was refluxed for 15 minutes in methanol (35 mL) and filtered obtaining 0.95 g (65% from IV) of (V; R'=$CF_3$), (HPLC: 94%, conditions as described in example 1);
$^1$H-NMR 200 MHz (in $CDCl_3$): $\delta=1.46$ (3H, s), 1.50-2.20 (3H, m), 2.68-3.27 (4H, m), 4.08 (4H, s) 7.60 (1H, d, J=8.1 Hz), 7.88 (1H, t, J=8.0 Hz), 8.48 (1H, dd, J=1.2;8.0 Hz), 13.45 (2H, s).
M.S : m/z=544 ($M^+$, base peak).
U.V. (in EtOH): $\lambda=531,496,255,206$ nm; $\lambda max=255$ nm.
I.R. (Nujol mull): $\nu=3525,1615,1585$ $cm^{-1}$.
$[\alpha]_D^{20}$ (c=0.1 in dioxane)= $-62.5°$
TLC on Kielsegel plate F 254 (Merck) using chlroform/acetone (9/1 by volume): Rf=0.58.

EXAMPLE 3

4-Demethyl-4-(4'fluorobenzensulfonyl)-7-deoxy-13-dioxolanyl daunomycinone (V; R'=4-F($C_6H_4$))

To a solution in pyridine (110 mL) of 1.1 g (2.7 mmol) of (IV), 2.3 mL (13.2 mmol) of diisopropylethylamine and 0.33 g (2.7 mmol) of 4-dimethylaminopyridine, cooled to 0° C. were added 0.58 g (3.0 mmol) of 4-fluorobenzensulfonyl chloride and the reaction mixture was stirred for 1 hour at room temperature. The reaction mixture was then cooled to 0° C. and added with 500 mL of methylene chloride and 300 mL of 10% hydrochloric acid. The organic phase was washed with water, dried over sodium sulfate and the solvent evaporated under reduced pressure. The residue was chromatographated on silica gel (toluene/acetone 8:2 by volume as eluant) obtaining 1.0 g (70.0% from IV) of (V, R'=4-F($C_6H_4$)), (HPLC: 98.3%);
$^2$H-NMR 300 MHz (in $CDCl_3$): $\delta=1.46$ (3H, s), 1.50-1.87 (2H, m), 2.05 (1H, dd, J=2.4;6.1 Hz), 2.70-3.18 (4H, m), 4.08 (4H, s), 7.10-7.25 (2H, m), 7.63 (1H, d, J=8.0 Hz), 7.78 (1H, t, J=8.0 Hz), 7.96-8.01 (2H, m), 8.37 (1H, dd, J=1.3;7.8 Hz), 13.39 (1H, s), 13.45 (1H, s).
M.S.:m/z=570 ($M^+$, base peak).
$[\alpha]_D^{20}$ (c=0.1 in dioxane)= $-34.4°$.
U.V. (in EtOH):$\lambda=528,493,254,206$ nm; $\lambda max=254$ nm.
I.R. (Nujol mull):$\nu=3500,1610,1580$ $cm^{-2}$.
TLC on Kieselgel plate F 254 (Merck) using chloroform/acetone (9/1 by volume): Rf=0.61.

EXAMPLE 4

4-Demethyl-4-(4'toluensulfonyl)-7-deoxy-13-dioxolanyl daunomycinone (V; R'=4—$CH_3$($C_6H_4$))

The synthesis was carried out as described in example 3 except that 4-toluensulfonyl chloride was used as sulfonating agent. The reaction crude was chromatographed on silica gel (toluene/acetone 8:2 by volume as eluant) obtaining 1.0 g (67.0% from IV) of (V, R'=4—$CH_3$($C_6H_4$)), (HPLC: 97.5%).
$^1$H-NMR 300 MHz (in $CDCl_3$): $\delta=1.46$ (3H, s), 1.50-1.85 (2H, m), 2.05 (1H, dd, J=2.4;6.1 Hz), 2.40 (3H, s), 2.70-3.14 (4H, m), 4.08 (4H, s), 7.30 (2H, d, J=8.4 Hz), 7.59 (1H, d, J=7.5 Hz), 7.76 (1H, t, J=7.9 Hz) 7.80 (2H, d, J=8.4 Hz), 8.36 (1H, dd, J=1.2;7.8 Hz), 13.40 (1H, s), 13.42 (1H, s).
M.S.: m/z=566 ($M^+$, base peak).
$[\alpha]_D^{20}$ (c=0.1 in dioxane)= $-68.1°$.

U.V. (in EtOH): λ=528,493,254,228,205 nm; λmax=254 nm.

I.R. (Nujol mull): $\nu$=3430,1610,1575 cm$^{-1}$.

TLC on Kieselgel plate F 254 (Merck) using chloroform/acetone (9/1 by volume): Rf=0.57.

EXAMPLE 5

4-Demethoxy daunomycinone (I, R=H)

To a solution of 2 g of (V; R'=CF$_3$), (3.6 mmol) in 50 mL of dimethylformamide under an inert atmosphere, were successively added 2 mL of triethylamine, 0.6 mL of formic acid, 110 mg of 1,1'-bis(diphenylphosphino) ferrocene (0.178 mmol) and 40 mg of palladium acetate (0.178 mmol). The reaction mixture was stirred for 30 minutes at 60° C., then cooled to 0° C., acidified with 10% hydrochloric acid and extracted with methylene chloride. The organic phase was evaporated to dryness and the residue chromatographated on silica gel (toluene/acetone 8:2 by volume as eluant) obtaining 1.24 g (86.9%) of 4-demethoxy-7-deoxy-13-dioxolanyl daunomycinone (VII; R=H), (HPLC: 98.4%).

$^1$H-NMR 200 MHz (in CDCl$_3$): δ=1.45 (3H, s), 1.6-2.15 (3H, m), 2.70-3.16 (4h, m), 4.08(4H, s), 7.76-7.85 (2H, m), 8.3-8.36(2 h. m), 13.52(1h, s), 13.54(1H, s).

M.S.: m/z=396 (M$^+$, base peak).

$[α]_D^{20}$ (c=0.1 in dioxane)=−52.5°.

U.V. (in EtOH): λ=516,482,288,252,204 nm; λmax=252.

I.R. (Nujol mull): $\nu$=3415,1612,1580 cm$^{-1}$.

TLC on Kieselgel plate F 254 (Merck) using chloroform/acetone (9/1 by volume): Rf=0.59.

The compound described above (VII, R=H), (1 g, 2.5 mmol) was dissolved in 160 mL of carbon tetrachloride, heated at reflux temperature and added with 2,2'-azo-isobutyronitrile (0.55 g) and 160 mL of water. To the reaction mixture, vigorously stirred, were added dropwise over 30 min. 4.8 mL of a 0.6M solution of bromine in carbon tetrachloride. After 1 hour the mixture was cooled and the organic phase was washed with water and extracted with 1N sodium hyroxide. The pH of the aqueous alkaline solution was adjusted to 8.2 with 2N hydrochloric acid and the mixture extracted with methylene chloride. The solution was dried over sodium sulfate and the solvent evaporated in vacuo. The residue was dissolved in 30 mL of trifluoroacetic acid and 3 mL of water at 0° C. and stirred for 1 hour; the reaction mixture was then diluted with 50 mL of water and extracted with methylene chloride. The organic phase was washed with aqueous sodium hydrogen carbonate and water and dried over sodium sulfate. The solvent was removed in vacuo and the residue chromatographated on silica gel (chloroform/acetone 9:1 by volume as eluant) obtaining 0.52 g (56.5% from VII, R=H) of (I, R=H), (HPLC: 99.1%), $^1$H-NMR 300 MHz (in CDCl$_3$): δ=2.19 (1H, dd, J=4.8,14.5 Hz), 2.37 (1H, ddd, J=2.0, 2.0, 14.5 Hz), 2.43 (3H, s), 2.95 (1H, d, J=18.6 Hz), 3.20 (1H, dd, J=2.0, 18.6 Hz), 3.83 (1H, d, J=4.8 Hz), 4.55 (1H, s), 5.32 (1H, ddd, J=2.0, 4.8, 4.8 Hz), 7.84-7.86 (2H, m), 8.33-8.36 (2H, m), 13.30 (1H, s), 13.60 (1H, s).

U.V. (in EtOH): λ=208,252,257,285,480,500,514 nm; λmax=252 nm.

I.R. (KBr pellet): $\nu$=3450, 1715, 1652, 1585 cm$^{-1}$.

$[α]_D^{20}$ (c=0.1 in dioxane)=+159°.

M.S.: m/z=368 (M$^+$, base peak).

TLC on Kieselgel plate F 254 (Merck) using chloroform/acetone (8:2 by volume): Rf=0.70.

EXAMPLE 6

4-Demethoxy daunomycinone (I; R=H)

The reaction was carried out as described in example 5 except that dioxane (50 mL) was used as solvent and 1,3-diphenylphosphinopropane (74 mg, 0.178 mmol) as ligand for palladium.

After 1 hour at 60° C. the reaction mixture was worked up as described in example 5 obtaining 1.17 g (82.0%) of 4-demethoxy-7-deoxy-13-dioxolanyl daunomycinone (VII; R=H), (HPLC 99.1%).

Compound (VII; R=H) was then converted into 4-demethoxy daunomycinone (I; R=H) as described in example 5.

EXAMPLE 7

4-Demethoxy daunomycinone (I; R=H)

The reaction was carried out as described in example 5 except that tri-p-tolylphosphine (108 mg, 0.356 mmol) was used as ligand for palladium. After 1 hour at 60° C. the reaction mixture was worked up as described in example 5 obtaining 1.21 g (84.8%) of 4-demethoxy-7-deoxy-13-dioxolanyl daunomycinone (VII; R=H), (HPLC 98.9%).

Compound (VII; R=H) was then converted into 4-demethoxy daunomycinone (I; R=H) as described in example 5.

EXAMPLE 8

4-Demethoxy daunomycinone (I; R=H)

The reaction was carried out as described in example 5 except that 4-demethyl-4-(4'fluorobenzensulfonyl)-7-deoxy-13-dioxolanyl daunomycinone (V; R'=4-F(C$_6$H$_4$)), (2.07 g, 3.6 mmol) was used as substrate. The reaction mixture was stirred for 7 hours at 90° C., then worked up as described in example 5 obtaining 1.05 g (73.6% 9 of 4-demethoxy-7-deoxy-13-dioxolanyl daunomycinone (VII; R=H), (HPLC: 98.7%).

Compound (VII; R=H) was then converted into 4-demethoxy daunomycinone (I; R=H) as described in example 5.

EXAMPLE 9

4-Demethoxy daunomycinone (I; R=H)

The reaction was carried out as described in example 5 except that 4-demethyl-4-(4'toluensulfonyl)-7-deoxy-13-dioxolanyl daunomycinone (V; R'=4—CH$_3$(C$_6$H$_4$)), (2.04 g, 3.6 mmol) was used as substrate, dioxane (50 mL) as solvent and 1,3-diphenylphosphinopropane (74 mg, 0.178 mmol) as ligand for palladium. The reaction mixture was stirred for 7 hours at 90° C., then worked up as described in example 5 obtaining 1.0 g (70%) of 4-demethoxy-7-deoxy-13-dioxolanyl daunomycinone (VII; R=H), (HPLC: 99.0%) Compound (VII; R=H) was then converted into 4-demethoxy daunomycinone (I; R=H) as described in example 5.

EXAMPLE 10

4-Demethoxy-4-methoxycarbonyl daunomycinone (I; R=COOCH$_3$)

To a solution of 2 g of (V; R'=CF$_3$), (3.6 mmol) in 50 mL of dioxane, under a carbon monoxide atmosphere, were successively added 1 mL of triethylamine, 3 mL of methanol. 74 mg of 1,3 diphenylphosphinopropane (0.178 mmol) and 40 mg of palladium acetate (0.178 mmol). The reaction mixture was stirred at 60° C. until the CO absorption stopped, then cooled to 0° C., acidified with 10% hydrochloric acid and extracted with methylene chloride. The organic phase was evaporated to dryness leaving 1.44 g (88.1%) of crude 4-demethoxy-4-methoxycarbonyl-7-deoxy-13-dioxolanyl daunomycinone (VII; R=COOCH3), (HPLC: 95.1%).

$^1$H-NMR 300 MHz (in CDCl3): δ=1.46 (3H,s), 1.58-1.90 (2H,m), 2.00-2.08 (1H,m), 2.75-3.12 (4H,m), 4.02 (3H,s), 4.06 (4H,s) 7.68 (1H,dd,J=7.5,1.3 Hz), 7.82 (1H,t,J=7.6 Hz), 8.41 (1H,dd,J=7.8,1.3 Hz), 13.07 (1H,s), 13.40 (1H,s).

U.V. (in EtOH): λ=523,489,256,206 nm; λmax=206 nm.

I.R. (Nujol mull): ν=3490,1725,1615,1570 cm$^{-1}$.

$[α]_D^{20}$ (c=0.1 in dioxane)=−51°.

M.S.: m/z=454 (M$^+$, base peak).

TLC on Kieselgel plate F 254 (Merck) using chloroform/acetone (9/1 by volume): Rf=0.54.

The compound described above (VII; R=COOCH3), (1.4 g; 3.08 mmol) was dissolved in 200 mL of carbon tetrachloride, heated at reflux temperature and added with 2,2'-azo-isobutyronitrile (0.68 g) and 200 mL of warer. To the reaction mixture, vigorously stirred, were added dropwise, over 30 min, 5.9 mL of a 0.6M solution of bromine in carbon tetrachloride. After 1 hour the mixture was cooled and the organic phase was washed with water and extracted with 1N sodium hydroxide. The pH of the aqueous alkaline solution was adjusted to 8.2 with 2N hydrochloric acid and the mixture extracted with methylene chloride. The solution was dried over sodium sulfate and the solvent evaporated in vacuo. The residue was dissolved in 37 mL of trifluoroacetic acid and 4 mL of water at 0° C. and stirred for 1 hour; the reaction mixture was then diluted with 60 mL of water and extracted with methylene chloride. The organic phase was washed with aqueous sodium hydrogen carbonate and water and dried over sodium sulfate. The solvent was removed in vacuo and the residue chromatographated on silica gel (chloroform/acetone 95:5 by volume as eluant) obtaining 0.71 g (54.1% from VII, R=COOCH3) of (I; R=COOCH3), (HPLC: 98.7%)

$^1$H-NMR 300 MHz (in CDCl3): δ=2.04 (1H, dd,J=14.5;4.7 Hz), 2.32 (1H,d,J=14.5 Hz), 2.45 (3H,s), 2.87 (1H,d,J=19 Hz), 3.08 (1H,dd,J=19;1.8 Hz), 4.02 (3H,s), 4.21 (1H,bs), 4.76 (1H,s), 5.21 (1H,bs), 7.71 (1H,dd,J=7.7; 1.2 Hz), 7.87 (1H,t,J=7.7 Hz), 8.38 (1H,dd,J=7.7;1.2 Hz), 12.88 (1H,s), 12.98 (1H,s).

U.V. (in EtOH): λ=522,489,461,285,253,206 nm; λmax=253 nm.

I.R. (Nujol mull): ν=3440,1735,1713,1622,1576 cm$^{-1}$.

$[α]_D^{20}$ (c=0.1 in dioxane)=+145°.

M.S. m/z=426 (M$^+$, base peak).

TLC on Kieselgel plate F 254 (Merck) using chloroform/acetone (9:1 by volume) Rf=0.40.

EXAMPLE 11

4-Demethoxydaunomycinone-4-carboxylic acid (I; R=COOH)

The reaction was carried out as described in example 10 except that 4-methoxybenzyl alcohol (9.8 g; 72 mmol) was used instead of methanol. After the CO absorption ceased the reaction mixture was worked up as described in example 10 to give 1.65 g (81.8%) of crude 4-demethoxy-4-(4'-methoxybenzyl)carbonyl-7-deoxy-13-dioxolanyl daunomycinone (VII; R=COOCH2 (C6H4)OCH3), (HPLC: 96.3%).

$^1$H-NMR 300 MHz (in CDCl3): δ=1.45 (3H,s), 1.60-2.10 (3H,m), 2.75-3.22 (4H,m), 3.95 (3H,s), 4.08 (4H,s), 5.23 (2H,s), 6.86 (2H,d,J=8.7 Hz), 7.39 (2H,d,J=8.7 Hz), 7.69 (1H,dd,J=7.5,1.3 Hz), 7.81 (1H,t,J=7.6 Hz), 8.38 (1H,dd,J=7.8,1.3 Hz), 13.03 (1H,s), 13.42 (1H,s).

U.V. (in EtOH): λ=522,488,257,206 nm; λmax=206 nm.

I.R. (Nujol mull): ν=3400,1730,1610,1570 cm$^{-1}$.

$[α]_D^{20}$ (c=0.1 in dioxane)=−58°.

M.S. m/z=560 (M$^+$, base peak).

TLC on Kieselgel plate F 254 (Merck) using chloroform/acetone (9/1 by volume): 0.55.

The compound described above (VII; R=COOCH2(C6H4)OCH3) was then converted into 4-demethoxydaunomycinone-4-carboxylic acid (I; R=COOH) as described in example 10.

$^1$H-NMR 300 MHz (in DMSO d6): δ=1.90-2.08 (1H,m), 2.20-2.28 (1H,m), 2.38 (3H,s), 2.96 (1H,d,J=18.7 Hz), 3.08 (1H,d,J=18.7 Hz), 5.10 (1H,bs), 5.38 (1H,d,J=6.6 Hz), 6.17 (1H, bs), 7.94 (1H,d,J=7.3 Hz), 8.07 (1H,t,J=7.6 Hz), 8.39 (1H,d,J=7.5 Hz), 13.15 (1H,s), 13.25 (1H,s), 13.40 (1H,bs).

U.V. (in EtOH): λ=486,287,251,205 nm; λmax=251 nm.

I.R. (Nujol mull): λ=3340,1695,1610,1565 cm$^{-1}$.

$[α]_D^{20}$ (c=0.1 in dioxane)=+146°.

M.S. m/z=412 (M$^+$, base peak).

We claim:

1. A process for the preparation of an anthracyclinone of formula (I):

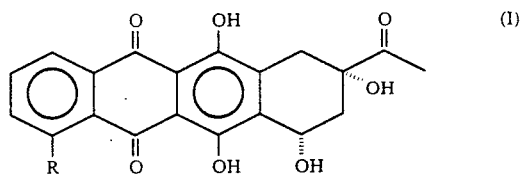

wherein R represents a hydrogen atom or a COOR$_1$ group in which R$_1$ is a hydrogen atom or a straight or branched alkyl group having from 1 to 10 carbon atoms optionally substituted at one or more carbon(s) in the chain by an aryl, alkoxy, ester or amide group, which process comprises:

(i) (a) reacting a 4-demethyl-4-sulfonyl-7-deoxy-13-dioxolanyl daunomycinone of formula (V):

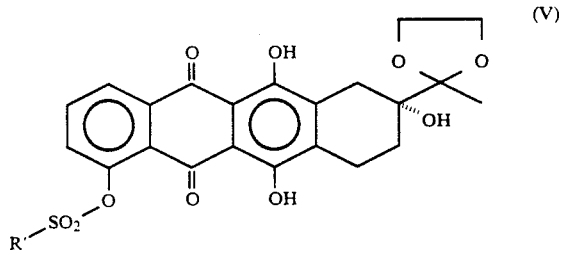

wherein R' represents an alkyl group having from 1 to 10 carbon atoms optionally substituted by one or more halogen atoms or an aryl group optionally substituted by halogen, alkyl, alkoxy or nitro, in a reducing environment with a catalytic amount of a compound of formula (VIII):

$$ML_nL'_m \quad \text{(VIII)}$$

wherein M represents a transition metal atom, L and L', which may be the same or different, each represent an anion or a neutral molecule selected from the group consisting of Cl, $CH_3COO$, monophosphine, di-phosphine, phosphite and diamine; and n and m may vary from 0 to 4, such as to obtain a compound of formula (VII):

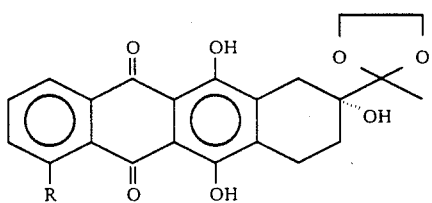

(VII)

wherein R represents hydrogen; or
(b) carbonylating a 4-demethyl-4-sulfonyl-7-deoxy-13-dioxolanyl daunomycinone of formula (V) as defined above, with carbon monoxide in the presence of a nucleophile $R_1OH$ wherein $R_1$ is as defined above, an organic or inorganic base and as catalyst a compound of formula (VIII) as defined above, such as to obtain a compound of formula (VII) as shown above wherein R represents a $COOR_1$ group; and
(ii) introducing an α-hydroxy group at the 7-position and removing the 13-oxo protecting group by acid hydrolysis from the resultant compound of formula (VII).

2. A process according to claim 1, wherein in step (i)(a) the daunomycinone of formula (V), dissolved in an appropriate solvent and under an inert atmosphere, is reacted at 60° C. with a reducing system composed of a trialkylammonium formate formed in situ by addition of formic acid and a trialkylamine.

3. A process according to claim 1, wherein in step (i)(b) the pressure of the carbon monoxide used for the carbonylation is from 1 to 100 atm.

4. A process according to claim 3, wherein the pressure is from 1 to 10 atm.

5. A process according to claim 1, wherein in step (i)(b) the base used is a trialkylamine or an alkali or alkaline earth metal carbonate or hydroxide.

6. A process according to claim 1, wherein in the catalyst of formula (VIII)

$$ML_nL'_m \quad \text{(VIII)}$$

M represents palladium or nickel, L and L' each independently represent $Cl^-$, $CH_3COO^-$, solvent molecule, a mono or di-phosphine, a phosphite or a diamine and m and n may vary from 1 to 4.

7. A process according to claim 1, wherein the catalyst of formula (VIII), with reference to the starting material of formula (V), is used in a molar ratio from 1:1 to 1:10000.

8. A process according to claim 7, wherein the molar ratio is from 1:20 to 1:1000.

9. A process according to claim 1, wherein the α-hydroxy group is introduced at the 7-position of the compound of formula (VII), the 13-dioxolanyl protecting group is removed by acid hydrolysis at 0° with trifluoroacetic acid, and the obtained crude product is purified by chromatography on a silica gel column using as eluent system chloroform-acetone.

* * * * *